(12) United States Patent
Nakamura et al.

(10) Patent No.: US 7,655,125 B2
(45) Date of Patent: Feb. 2, 2010

(54) ELECTROPHORESIS APPARATUS

(75) Inventors: Shin Nakamura, Kyoto (JP); Rintaro Yamamoto, Kyoto (JP); Akira Harada, Kyoto (JP); Makoto Hazama, Kyoto (JP); Takashi Ikegami, Kyoto (JP); Toru Kaji, Kyoto (JP); Naoya Endo, Kyoto (JP); Hidesato Kumagai, Kyoto (JP); Tetsuo Ohashi, Kyoto (JP); Atsushi Inami, Kyoto (JP); Keisuke Miyamoto, Kyoto (JP); Shinichi Utsunomiya, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 290 days.

(21) Appl. No.: 11/905,539

(22) Filed: Oct. 2, 2007

(65) Prior Publication Data

US 2008/0087547 A1    Apr. 17, 2008

(30) Foreign Application Priority Data

Oct. 3, 2006    (JP) .............................. 2006-271397

(51) Int. Cl.
*G01N 27/453* (2006.01)
(52) U.S. Cl. ...................................... 204/604; 204/601
(58) Field of Classification Search ......... 204/601–605, 204/451–455; 422/99, 100
See application file for complete search history.

(56) References Cited

U.S. PATENT DOCUMENTS 6,787,111 B2 * 9/2004 Roach et al. ................. 422/99

| | | |
|---|---|---|
| 2002/0046949 A1 | 4/2002 | Nakamura et al. |
| 2003/0102219 A1 | 6/2003 | Yamamoto et al. |
| 2006/0191793 A1 | 8/2006 | Yamamoto |
| 2006/0201809 A1 | 9/2006 | Endo et al. |
| 2009/0107843 A1 * | 4/2009 | Hanafusa et al. ............ 204/600 |

FOREIGN PATENT DOCUMENTS

| JP | 2004-251680 A | 9/2004 |
|---|---|---|
| WO | WO-02/49761 A2 | 6/2002 |

OTHER PUBLICATIONS

European Search Report for Application No. EP 07 01 9282, dated Jan. 10, 2008.
Database WPI Week 200465, Derwent Publications Ltd., London, BG, AN: 2004-664022, Doc. No. XP002463285.

* cited by examiner

*Primary Examiner*—Alex Noguerola
(74) *Attorney, Agent, or Firm*—Cheng Law Group, PLLC

(57) ABSTRACT

For automating the operation of an electrophoresis apparatus and improving the throughput, the present electrophoresis apparatus has two platens capable of controlling temperature of electrophoresis plates placed thereon, a loading medium charging unit for sending a loading medium under pressure, a loading medium charging nozzle mechanism having a pair of nozzles connected to the loading medium charging unit, a pipetter mechanism for dispensing samples to sample dispensing openings of the electrophoresis plates placed on the platens, a stacker mechanism for storing sample plates, a loading buffer solution supplying mechanism, a loading buffer solution dispensing mechanism connected to the loading buffer solution supplying mechanism, a power unit for allowing electrophoresis separation for each electrophoresis plate placed on the platens, and a detector for optically detecting components migrating through each electrophoresis flow channel of the electrophoresis plates.

14 Claims, 12 Drawing Sheets

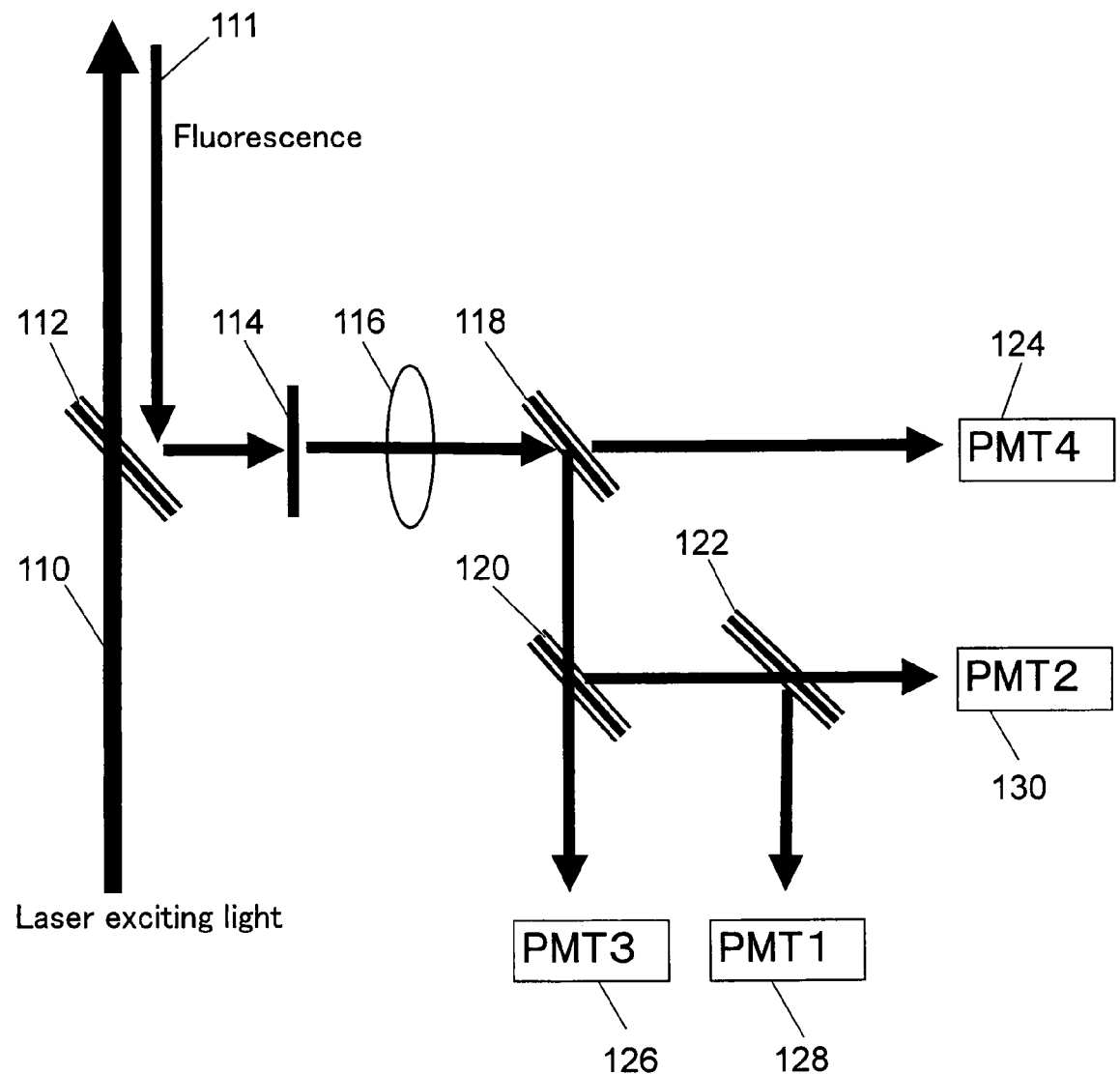

ELECTROPHORESIS APPARATUS

BACKGROUND OF THE INVENTION

1. Field of the Invention

The present invention relates to an electrophoresis apparatus which analyzes a trace amount of protein, nucleic acid, drug and the like at high speed and with high resolution in biochemical, molecular biological or clinical fields, for example, in DNA sequencing.

2. Description of the Related Art

Conventionally, for analyzing a trace amount protein or nucleic acid, an electrophoresis apparatus is used. One typical electrophoresis apparatus is a capillary electrophoresis apparatus. The capillary electrophoresis apparatus; however, has a drawback of complicated handling. In order to speed up the analysis and downsize the apparatus, while overcoming the above drawback of the capillary electrophoresis apparatus, an electrophoresis member having a flow channel built in a substrate is proposed.

In an early electrophoresis apparatus, an electrophoresis member having only one electrophoresis flow channel is used, and afterward, an electrophoresis plate having a plurality of electrophoresis flow channels for improving the throughput is proposed (Japanese Patent Application Laid-Open Publication No. 2004-251680).

In such an electrophoresis plate, two glass substrates are joined and a plurality of very fine electrophoresis flow channels are formed in the joining face.

However, there are a lot of problems to be solved for automating a series of operations for electrophoresis separation such as charging of a loading medium into the electrophoresis flow channels, dispensing of a loading buffer solution to both end parts of the electrophoresis flow channels, dispensing of a sample to one end of each of the electrophoresis flow channels, and application of voltage for electrophoresis separation in the electrophoresis flow channels, using such an electrophoresis plate as described above, and a practically useful electrophoresis apparatus realizing high throughput has not been realized.

SUMMARY OF THE INVENTION

It is an object of the present invention to provide an electrophoresis apparatus running by automated operation and realizing high throughput.

An electrophoresis plate used in the present invention has a substrate with a plurality of electrophoresis flow channels formed therein, and a pair of cathode-side and anode-side reservoirs disposed at both end parts of the electrophoresis flow channels, which hold a loading buffer solution and electrically communicate at their bottom parts with the end parts of the electrophoresis flow channels via the loading buffer solution. Sample dispensing openings leading to first ends of the electrophoresis flow channels are disposed within the cathode-side reservoir. A loading medium charging groove leading to second ends of the electrophoresis flow channels is formed within the anode-side reservoir, and ports opening into the anode-side reservoir are formed on both ends of the loading medium charging groove.

The electrophoresis apparatus of the present invention includes two platens on which such an electrophoresis plate can be respectively placed, capable of controlling temperature of the placed electrophoresis plates; a loading medium charging unit for sending a loading medium under pressure; and a loading medium charging nozzle mechanism connected to the loading medium charging unit for charging the loading medium to the electrophoresis plates; a pipetter mechanism for dispensing samples to the electrophoresis plates; a stacker mechanism for storing sample plates holding samples, and sending out one selected sample plate to a sample aspirating position; a loading buffer solution supplying mechanism for supplying a loading buffer solution; a loading buffer solution dispensing mechanism connected to the loading buffer solution supplying mechanism, for dispensing the loading buffer solution to the electrophoresis plates; a power unit that applies voltage to the electrophoresis flow channels for each of the electrophoresis plates placed on the platens to cause electrophoresis separation; and a detector that optically detects components migrating along each electrophoresis flow channel at a detecting position set for the anode side of the electrophoresis plates placed on the two platens.

The loading medium charging nozzle mechanism has a pair of nozzles inserted into ports of the loading medium charging groove in the electrophoresis plates placed on the platens in a liquid-tight manner, and supports the nozzles movably between port positions of the electrophoresis plates placed on the two platens.

The pipetter mechanism includes a plurality of pipettes for dispensing samples to the sample dispensing openings of the electrophoresis plates placed on the platens, and a displacement mechanism that displaces the pipettes between a position of the sample dispensing openings of the electrophoresis plates placed on the two platens and a sample aspirating position at which samples are aspirated from the sample plate.

The loading buffer solution dispensing mechanism may have a loading buffer solution applying nozzle for applying the loading buffer solution to a reservoir of the electrophoresis plate placed on the platen, and may support the loading buffer solution applying nozzle so as to be movable between the reservoirs of the electrophoresis plates placed on the two platens.

In the electrophoresis apparatus of the present invention, the two platens are provided with an electrophoresis plate respectively, and electrophoresis separation may be executed alternately in the two electrophoresis plates. In the electrophoresis, substantially equivalent time is required for a so-called pretreatment including charging of a loading medium, pre-loading (preliminary electrophoresis carried out without applying samples) and application of samples, and for the process of electrophoretically separating the samples by application of voltage to the electrophoresis flow channels. Therefore, in the present electrophoresis apparatus, by conducting a pretreatment in one of the electrophoresis plates while conducting electrophoresis in the other one of the electrophoresis plates, it is possible to continuously execute the electrophoresis operation alternately in two electrophoresis plates. As a result, the throughput is improved almost twice compared to the case where an apparatus capable of mounting only one electrophoresis plate is used.

Preferably, a pitch at which the sample dispensing openings are arranged in the electrophoresis plate is 1/n (n is an integer) of a pitch of sample holding wells of the sample plate being used. In dispensing samples from a sample plate to a electrophoresis plate by the pipetter mechanism, it is possible to directly convey the samples aspirated by a plurality of pipettes to the sample dispensing position of the electrophoresis plate and apply thereto if the pitch at which the sample dispensing openings are arranged in the electrophoresis plate is 1/n of the pitch of sample holding wells of the sample plate being used. Therefore, throughput of the sample dispensing operation is improved.

Preferably, the platens and the electrophoresis plates are provided with a mark or a mechanism for mutual positioning.

If the platens and the electrophoresis plates are provided with a mark or a mechanism for mutual positioning, positioning in mounting an electrophoresis plate on a platen is facilitated.

One preferred form of the loading medium charging unit is adapted to receive a cartridge holding a loading medium attached thereto, and the cartridge has in its upper part, a plunger lid connected to the nozzle of the loading medium charging nozzle mechanism. The loading medium in the cartridge is sent under pressure by the plunger lid being relatively pushed down into the cartridge main body. The loading medium charging unit has a mechanism of fixing the plunger lid and a charging lift arm for pushing up the cartridge main body so as to push down the plunger lid relatively into the cartridge main body. When the loading medium charging unit to which a cartridge holding the loading medium is attached and which sends the loading medium in the cartridge under pressure is used, operability for charging the loading medium is improved.

The charging lift arm may have a load cell in an abutment portion on the cartridge main body side, and detect pressure during charging of the loading medium by the load cell. Generally, for monitoring abnormality occurring in the flow path before the loading medium leaving the cartridge is applied to the electrophoresis plate, pressure is detected. However, in this case, providing the charging lift arm with a load cell will eliminate the necessity of providing the flow path with a branch for attachment of a pressure sensor, will simplify the structure, and will facilitate washing in the flow channel, compared to the case of providing the flow channel with a pressure sensor.

One preferred form of the detector includes a spinner head having a lens constituting an epi-illumination optical system that focuses and projects exciting light to each electrophoresis flow channel in the detecting positions of the electrophoresis plates placed on the platens, and receives fluorescence generated from the components moving along each electrophoresis flow channel upon irradiation with the exciting light; a scanning mechanism that causes the spinner head to move reciprocatingly along an arc in a plane which is parallel with the electrophoresis plate so that it traverses the electrophoresis flow channels; an exciting optical system for generating the exciting light; and a light-receiving optical system for receiving fluorescence and detecting it while separating into four kinds of wavelengths. The scanning mechanism for reciprocatingly moving the spinner head has a hollow servo motor having a hollow space as its rotation axis as a driving source of the reciprocating movement, and the hollow space of the hollow servo motor forms an optical path connecting the spinner head to the exciting optical system and the light-receiving optical system. When the one that causes a spinner head having a lens forming an epi-illumination optical system to reciprocatingly move along an arc is used as the detector, the scanning mechanism that causes to move reciprocatingly along the arc may be achieved only by attaching the spinner head to the rotary mechanism. Therefore, the structure of the mechanism is simplified in comparison with the scanning system that reciprocatingly moves on a straight line, and the scanning speed can be readily improved. Further, when the exciting optical system and the light-receiving optical system are adapted to move in association with movement of the spinner head, the detector becomes bulky and operation at high speed becomes difficult; however, it is possible to miniaturize the detector by arranging the exciting optical system and the light-receiving optical system in different positions, using a hollow servo motor as a driving source of the scanning mechanism, and linking the spinner head to the exciting optical system and the light-receiving optical system while utilizing the hollow space of the hollow servo motor as an optical path.

As a light source of the exciting optical system, laser, for example, may be used.

One preferred form of the light-receiving optical system has one rejection filter for removing an exciting light component and three dichroic mirrors for separating into four kinds of wavelengths. When the light-receiving optical system of the detector has one rejection filter for removing an exciting light component and three dichroic mirrors for separating into four kinds of wavelengths, it is possible to identify the four kinds of bases and determine base sequences using this electrophoresis apparatus.

One preferred form of the pipetter mechanism is so designed that a disposable dispensing tip is detachably attached to each pipette, and has a detaching mechanism for detaching the dispensing tips from the pipettes. The displacement mechanism of the pipetter mechanism is able to displace the pipettes to both positions where the dispensing tips are arranged and where the dispensing tips are disposed. In this manner, at the position where the dispensing tips are arranged, the dispensing tips are attached to the pipettes by descending the pipettes toward the dispensing tips, while at the position where the dispensing tips are disposed, the dispensing tips are detached from the pipettes by the detaching mechanism. Providing the pipetter mechanism with a detaching mechanism for detaching dispensing tips from pipettes enables automation of the detaching operation of the dispensing tips in the pipetter mechanism.

Preferably, a wash port of automatic water feed type for washing the dispensing tips attached to the pipetter mechanism is further provided. Providing the wash port of automatic water feed type for washing the dispensing tips attached to the pipetter mechanism enables automatic washing of the dispensing tips.

One preferred form of the sample plate stored in the stacker mechanism is the one whose surface is covered with a sealing member for preventing vaporization of the samples. Preferably, the stacker mechanism has a punching mechanism that punches the sealing member in transferring such a sample plate to the sample aspirating position. By using the sample plate whose surface is covered with the sealing member for preventing vaporization of the samples, it is possible to prevent the samples from vaporizing even when a considerable time is taken until the samples are dispensed to the electrophoresis plate after receiving the samples in the sample plate. Therefore, since it is possible to prepare a plurality of sample plates holding samples in advance and store them in the stacker mechanism, it is also possible to analyze plural samples successively and to improve the throughput.

Preferably, the sample plate stored in the stacker mechanism has a barcode representing information about the samples, pasted thereto, and in such a case, the electrophoresis apparatus further includes a barcode reading mechanism that reads the barcode. When the barcode representing information about the sample is pasted to the sample plate, and the barcode is read by the barcode reading mechanism, data throughput improves.

Examples of liquid sending means in the loading buffer solution supplying mechanism include, but are not limited to, a peristaltic pump. Since accuracy of liquid sending is not required as the liquid sending means in the loading buffer solution supplying mechanism, use of the peristaltic pump contributes miniaturization of the apparatus.

Preferably, the loading buffer solution dispensing mechanism has a liquid level sensing means. Examples of the liquid level sensing means include, but are not limited to, a capacitance type liquid level sensor made up of two dielectric plate members. When the loading buffer solution dispensing mechanism has a liquid level sensing means, it is possible to control unnecessary supply of the loading buffer solution. Use of the capacitance type liquid level sensor as the liquid level sensing means simplifies the mechanism.

Preferably, the loading buffer solution dispensing mechanism has a heating and temperature control mechanism in the course of a flow channel through which the loading buffer solution is sent. When the loading buffer solution dispensing mechanism has the heating and temperature control mechanism in the course of a flow channel through which the loading buffer solution is sent, it is possible to make the temperature of the loading buffer solution to be dispensed to the electrophoresis plate coincident with the controlled temperature of the platens, so that a result having higher reproducibility can be obtained by preventing disorder of the electrophoresis speed at the start of electrophoresis.

BRIEF DESCRIPTION OF THE DRAWINGS

FIG. 10 is a schematic structure view showing an exciting optical system and a light-receiving optical system.

DETAILED DESCRIPTION OF THE INVENTION

Figure 1:
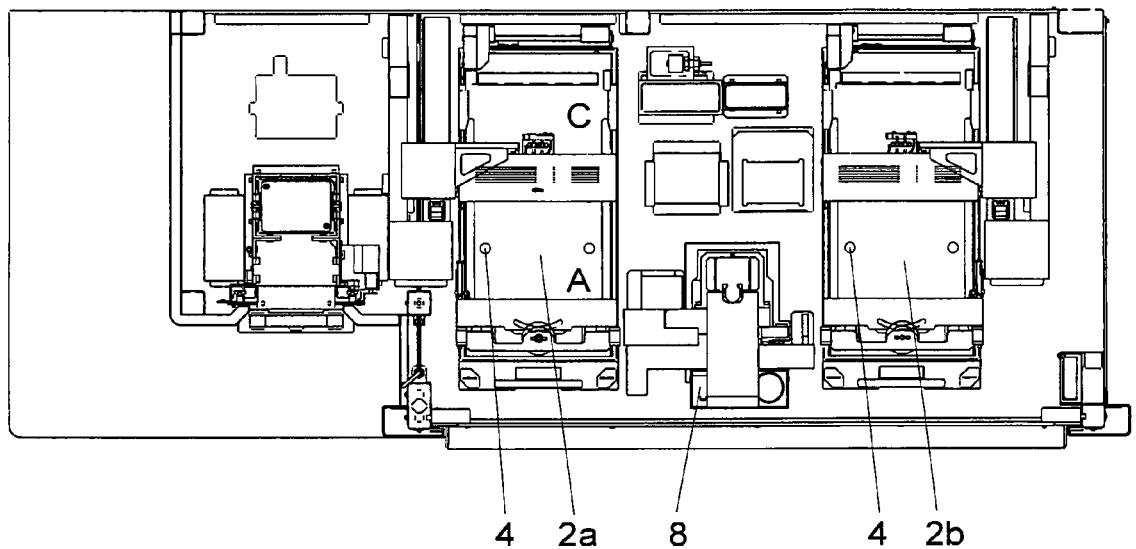
FIG. 1 is a top view showing the entirety of one exemplary embodiment
Figure 2:
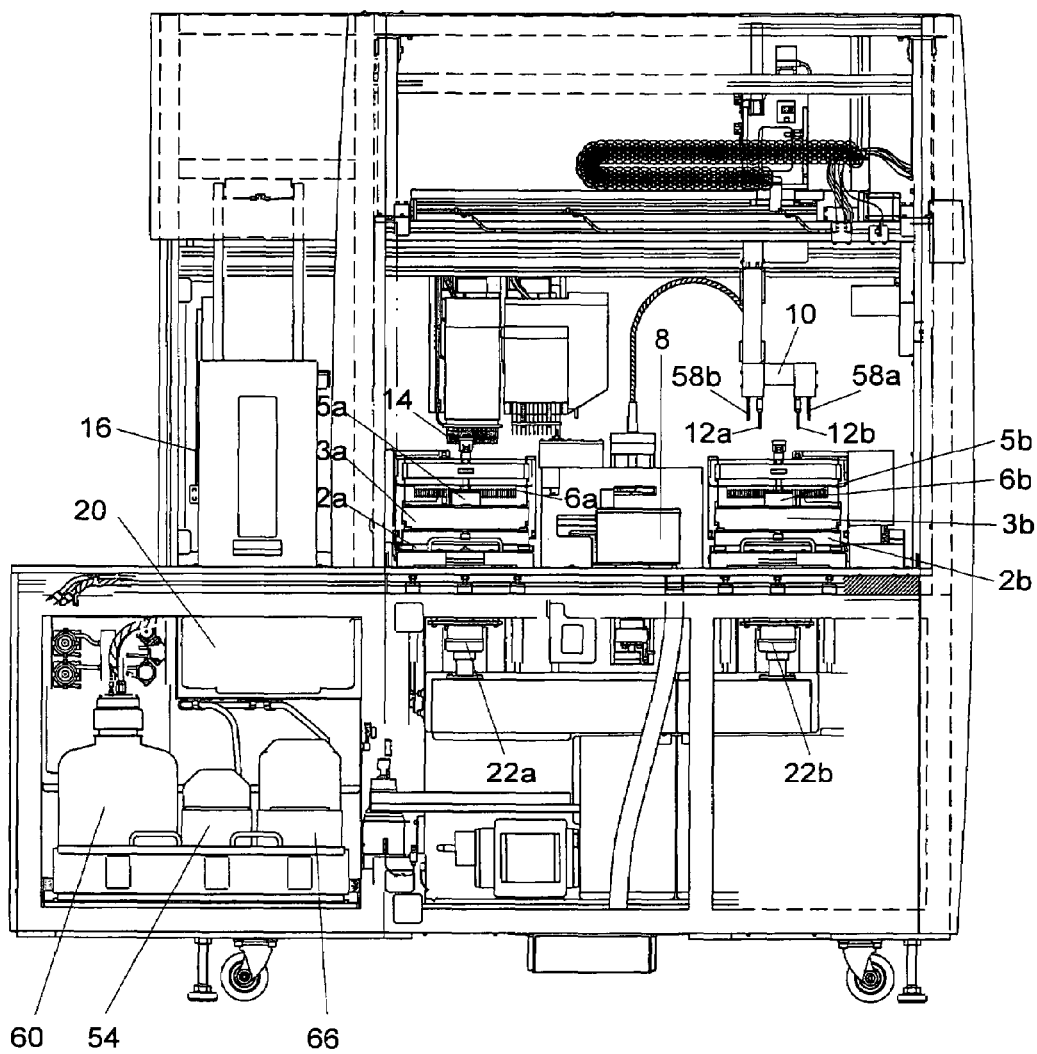
FIG. 2 is a front view showing the entirety of the same embodiment.

FIG. 1 and FIG. 2 show the entirety of the present electrophoresis apparatus, in which FIG. 1 is a top view and FIG. 2 is a front view. In a center part, two platens $2a$, $2b$ for mounting electrophoresis plates are arranged parallel with each other at the same height. Surfaces of the platens $2a$, $2b$ are made of black aluminum (a black anodic coating layer is formed on aluminum by anodizing), and are flat surfaces that hold the electrophoresis plates.

On the bottom face side of the platens $2a$, $2b$, a rubber heater and a temperature measuring resistor serving as a temperature sensor are incorporated, which enable heating and temperature control for keeping temperature of the electrophoresis plate constant during electrophoresis.

In the surfaces of the platens $2a$, $2b$, marks 4 are provided for positioning in mounting a plate. Each of the platens $2a$, $2b$ are provided with two marks 4 each, and the electrophoresis plates are also provided with marks for positioning in correspondence with these marks 4. By registering the marks by visual observation or by means of a machine, it is possible to place the electrophoresis plates in proper positions on the platens $2a$, $2b$.

As to the platens $2a$, $2b$, the front side of FIG. 1 is anode side, the back side is cathode side, and the direction directing from the cathode to the anode is the direction of electrophoresis. On the anode side, anode electrodes incorporated in anode reservoirs $3a$, $3b$ are provided, while on the cathode side, cathode electrodes $6a$, $6b$ in the shape of a pin holder in which electrodes are arranged at intervals corresponding to the arrangement intervals of sample dispensing openings are disposed respectively for the platens $2a$, $2b$ and are set to the electrophoresis plates in a detachable manner, whereby electrophoresis is carried out concurrently in both of the platens $2a$, $2b$.

The anode reservoirs $3a$, $3b$ are each implemented by a detachable resin container (for example, made of acrylic resin) having openings on the top and bottom parts, and in each bottom opening, an O-ring is attached on its circumference, and the anode reservoirs $3a$, $3b$ are pushed against the electrophoresis plates by fixing mechanisms ($5a$, $5b$). As a result, the anode reservoirs $3a$, $3b$ are connected while their bottom openings are kept liquid tight with the openings on the anode side of the electrophoresis plates by the O-rings.

In the front side of the center part, a loading medium charging unit 8 for sending a loading medium (gel) under pressure is provided. To the loading medium charging unit 8, two cartridges holding the loading medium may be attached. The details of the cartridges will be explained later by referring to FIGS. 6A and 6B. The reference numeral 10 denotes a loading medium charging nozzle mechanism connected to the loading medium charging unit 8. The loading medium charging nozzle mechanism, the details of which will be described later, has a pair of nozzles $12a$, $12b$ to be inserted into ports of a loading medium charging groove of electrophoresis plates placed on the platens $2a$, $2b$ in a liquid-tight manner, and these nozzles $12a$, $12b$ are movably supported between the electrophoresis plates placed on the two platens $2a$, $2b$.

Above the platens $2a$, $2b$, a pipetter mechanism 14 is disposed. The pipetter mechanism 14, the details of which will be described later with reference to FIGS. 8A and 8B, has a plurality of pipettes for dispensing samplea to the sample dispensing openings of the electrophoresis plates placed on the platens $2a$, $2b$, and also has a displacement mechanism that displaces these pipettes between positions of sample dispensing openings of the electrophoresis plates placed on the two platens $2a$, $2b$ and a sample aspirating position at which samples are aspirated from the sample plate.

On the lateral side of the platens $2a$, $2b$, a stacker mechanism 16 is disposed. The stacker mechanism 16 stores sample plates holding samples, and has a mechanism that sends out a selected one sample plate to the sample aspirating position and positions it.

A surface of a sample plate stored in the stacker mechanism 16 is covered with a sealing member for preventing vaporization of the samples, and the stacker mechanism 16 has a punching mechanism (not illustrated) for punching the sealing member of the sample plate in conveying the sample plate to the sample aspirating position.

A sample plate stored in the stacker mechanism 16 has a barcode showing information about the sample, pasted thereto, and the electrophoresis apparatus is provided with a barcode reading mechanism (not shown) for reading the barcode when the sample plate is conveyed from the stacker mechanism 16 to the sample aspirating position.

A loading buffer solution is held in a buffer solution tank 54, and is sent by a peristaltic pump serving as a loading buffer solution supplying mechanism in a pump mechanism 20.

As a loading buffer solution dispensing mechanism for dispensing the loading buffer solution to the electrophoresis plates placed on the platens 2a, 2b, a loading buffer solution applying nozzle 58a is provided, which is connected to the peristaltic pump of the loading buffer solution supplying mechanism and attached to the loading medium charging nozzle mechanism 10. The nozzle 58a is attached to the loading medium charging nozzle mechanism 10, so that it is movably supported between reservoirs of electrophoresis plates placed on the two platens 2a, 2b.

On the cathode side, a power unit (not illustrated) having an electrode arranged to be movable in the vertical direction is provided above each of the platens 2a, 2b, and such an electrode is inserted into the cathode-side reservoir of the electrophoresis plate on each of the platens 2a, 2b. On the anode side, an electric connection with electrophoresis flow channels of the electrophoresis plates is established by the electrodes incorporated in the anode reservoirs 3a, 3b via the loading buffer solution.

On the anode side, an optical detector that carries out optical detection through an opening provided in each of the platens 2a, 2b is arranged below the platens 2a, 2b for each platen. The optical detector, the details of which will be described later by way of FIGS. 9A to 9C, irradiates a detecting position of the electrophoresis plate with exciting light, and detects fluorescence from the samples that have migrated to that position. The reference numerals 22a, 22b denote hollow servo motors forming the respective scanning mechanisms of the detectors.

In the following, each part of the electrophoresis apparatus and the electrophoresis plate used therein will be explained in detail. FIG. 3A, FIG. 3B, FIG. 3C and FIG. 4A, FIG. 4B, FIG. 4C show one example of the electrophoresis plate used in the present electrophoresis apparatus.

Figure 3A:
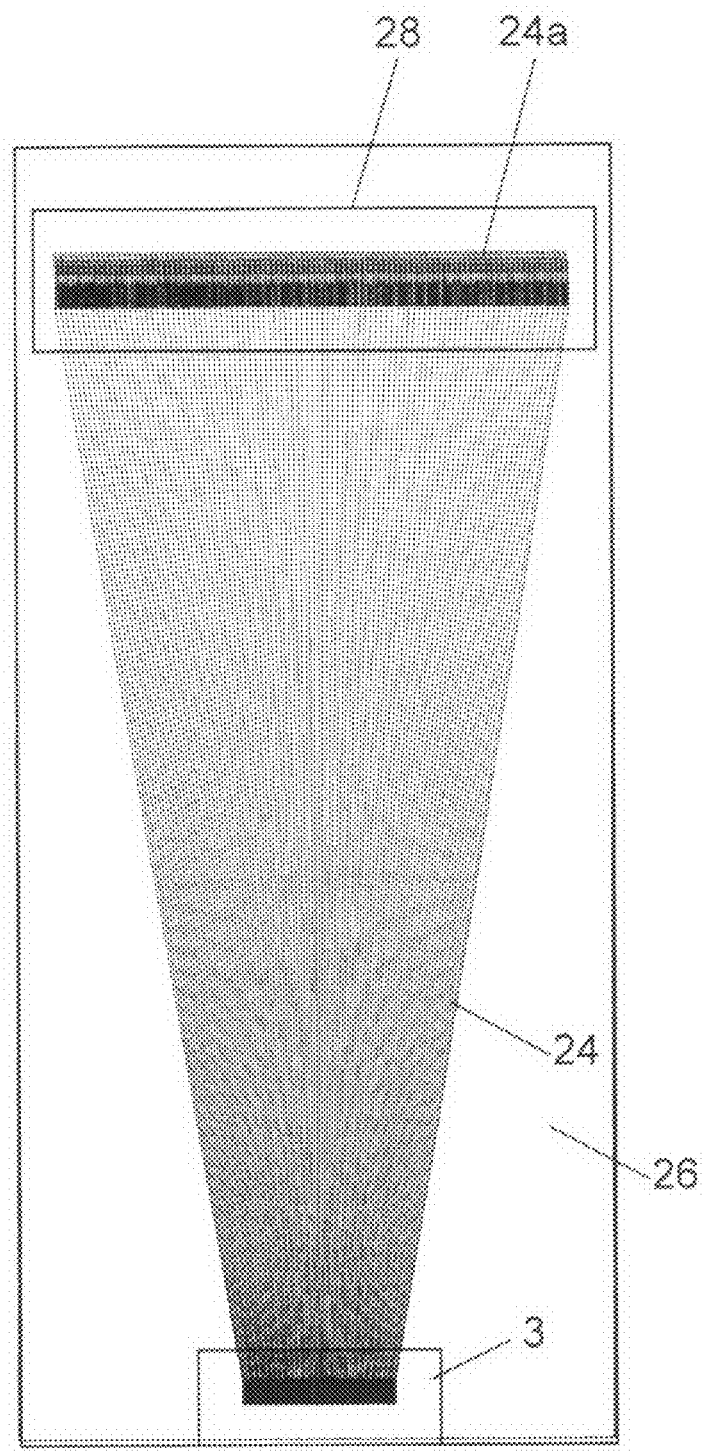
FIG. 3A is a plan view showing an electrophoresis plate used in the same embodiment.

As is schematically shown in FIG. 3A, a plurality of electrophoresis flow channels 24 are arranged so that they do not cross each other in a glass substrate 26, and the surface of the glass substrate 26 is attached with a reservoir 28 at an end part of the cathode side of the electrophoresis flow channels 24, and with a reservoir 3 (collective term for anode reservoirs 3a, 3b illustrated in FIG. 2) at an end part of the anode side in setting of the apparatus. Each electrophoresis flow channel 24 is 90 μm wide and 40 μm deep, and extends in the longitudinal direction of the glass substrate 26, and 384 of these channels are arranged in a radial region expanding from the cathode side to the anode side so that they do not cross each other.

Each of the reservoirs 28 and 3 forms a container having an opening top, holds the loading buffer solution, and is electrically communicable at its bottom part with end parts of the electrophoresis flow channels 24 via the loading buffer solution.

Figure 3B:
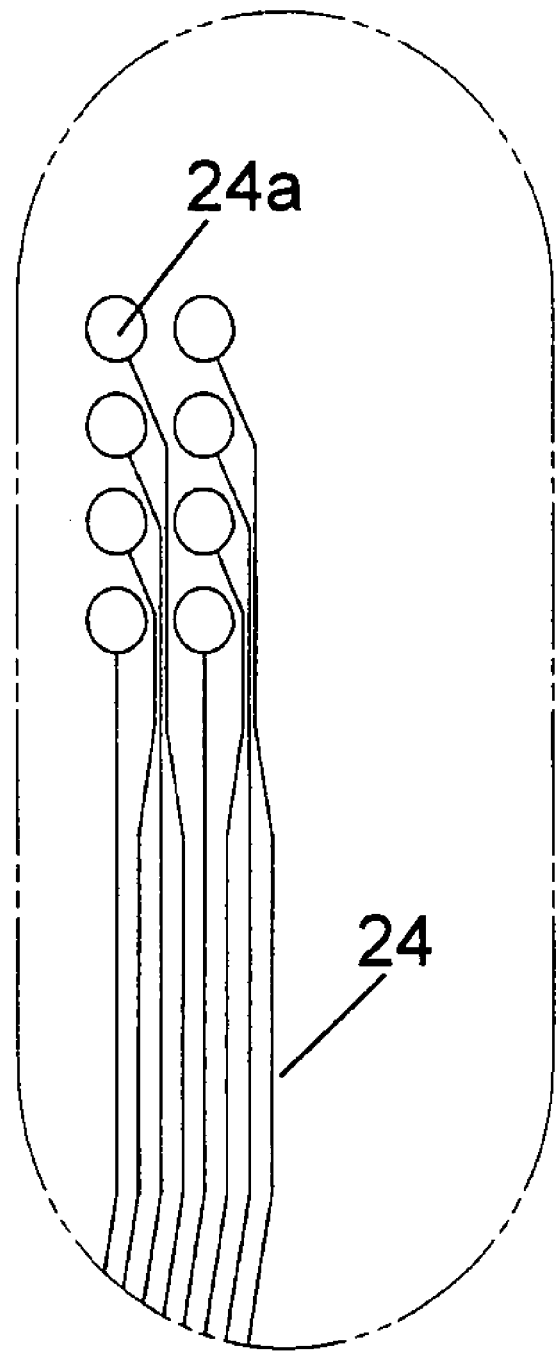
FIG. 3B is a partial plan view showing a part of openings disposed on a bottom part of a cathode-side reservoir of the same electrophoresis plate.
Figure 3C:
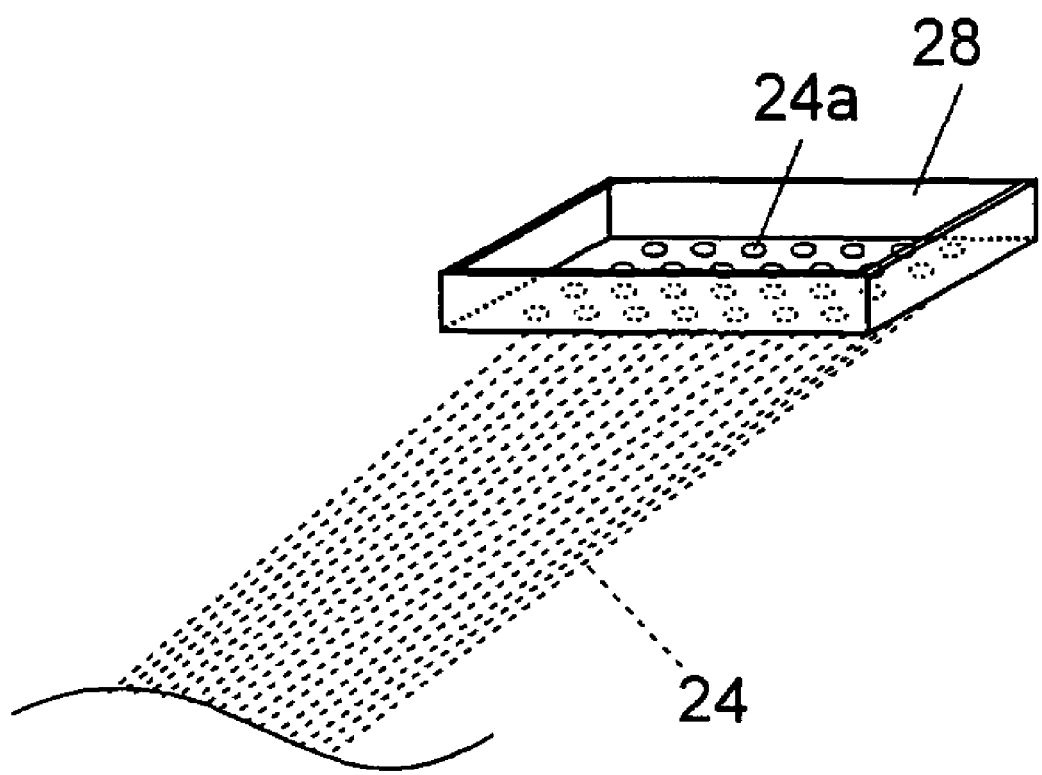
FIG. 3C is a perspective view showing the same cathode-side reservoir.

As shown in FIG. 3B, in the bottom part of the cathode-side reservoir 28, 384 openings 24a that lead to first ends of the electrophoresis flow channels 24 are arranged, and these openings 24a serve as the sample dispensing positions. The openings 24a are arranged in this case, at the same pitch with that of the wells holding the samples in the sample plate. However, the pitch may be 1/n of the arrangement pitch of wells. The reservoir 28 is a single container that surrounds the area where all of the openings 24a are arranged as shown in FIG. 3C which is a perspective view. The electrophoresis flow channels 24 are electrically connected with an electrode inserted into the reservoir 28 via the buffer solution within the reservoir 28.

Figure 4A:
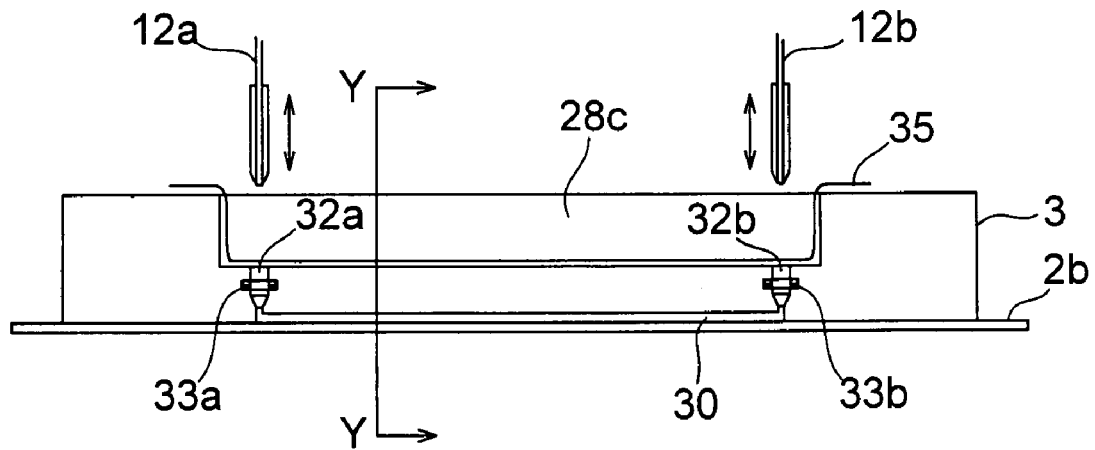
FIG. 4A is a section view of an anode-side reservoir shown together with a nozzle of a loading medium charging line.
Figure 4B:
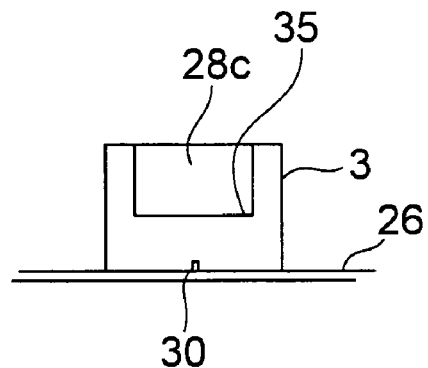
FIG. 4B is a section view along the line Y-Y of FIG. 4A.
Figure 4C:
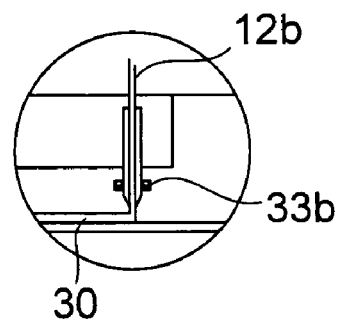
FIG. 4C is a section view showing the state in which the loading medium charging line is connected to the reservoir.

FIG. 4A, FIG. 4B and FIG. 4C show the anode-side reservoir 3. FIG. 4A is a section view of the reservoir 3, FIG. 4B is a section view along the line Y-Y of FIG. 4A, and FIG. 4C is a section view showing the state that a loading medium charging line is connected. In this description, the anode reservoir and the electrophoresis plate are collectively called the "anode reservoir 3" for simplification. However, the anode reservoir 3 is placed on the electrophoresis plate in a detachable manner, and a bottom opening of the anode reservoir 3 is connected to the anode-side opening of the electrophoresis plate via an O-ring while liquid tightness is kept therebetween. The reservoir 3 has, in its bottom part, a loading medium charging groove 30 consisting of a flow channel leading to the second ends of the electrophoresis flow channels 24, and at both ends of the loading medium charging groove 30, ports 32a, 32b that are open into the reservoir 3 are formed. In these ports 32a, 32b, O rings 33a, 33b are provided so that the nozzles 12a, 12b may be inserted in a liquid-tight manner. Also, the reservoir 3 is a container surrounding the area where openings of the second ends of all of the electrophoresis flow channels 24 are disposed. The electrophoresis flow channels 24 are electrically connected with a power unit via an electrode 35 fixed in the reservoir 3 and the buffer solution in the reservoir 3.

The nozzles 12a, 12b of the loading medium charging line are respectively inserted into the ports 32a, 32b in a detachable manner, and sealed with the O-rings 33a, 33b as shown in FIG. 4C so that the loading medium will not leak when it is supplied under pressure.

As a material for making the glass substrate 26, quartz glass or borosilicate glass may be used, and other materials such as resin may be used in place of the glass substrate 26. In this context, the glass substrate 26 of transparent material is selected for optically detecting the components separated by electrophoresis. However, the material of the glass substrate 26 is not limited to a transparent material when a detecting means other than an optical detector is used.

The glass substrate 26 may be made up of two glass plates bonded with each other. The electrophoresis flow channels 24 may be formed on a bonding surface of one of the glass plates by lithography and etching (wet etching or dry etching). The opening 24a or the like may be formed as a through-hole in the positions of both ends of the electrophoresis flow channels 24, in the other glass plate, or in the same glass plate by a technique such as sand blasting or laser drilling.

Figure 5:
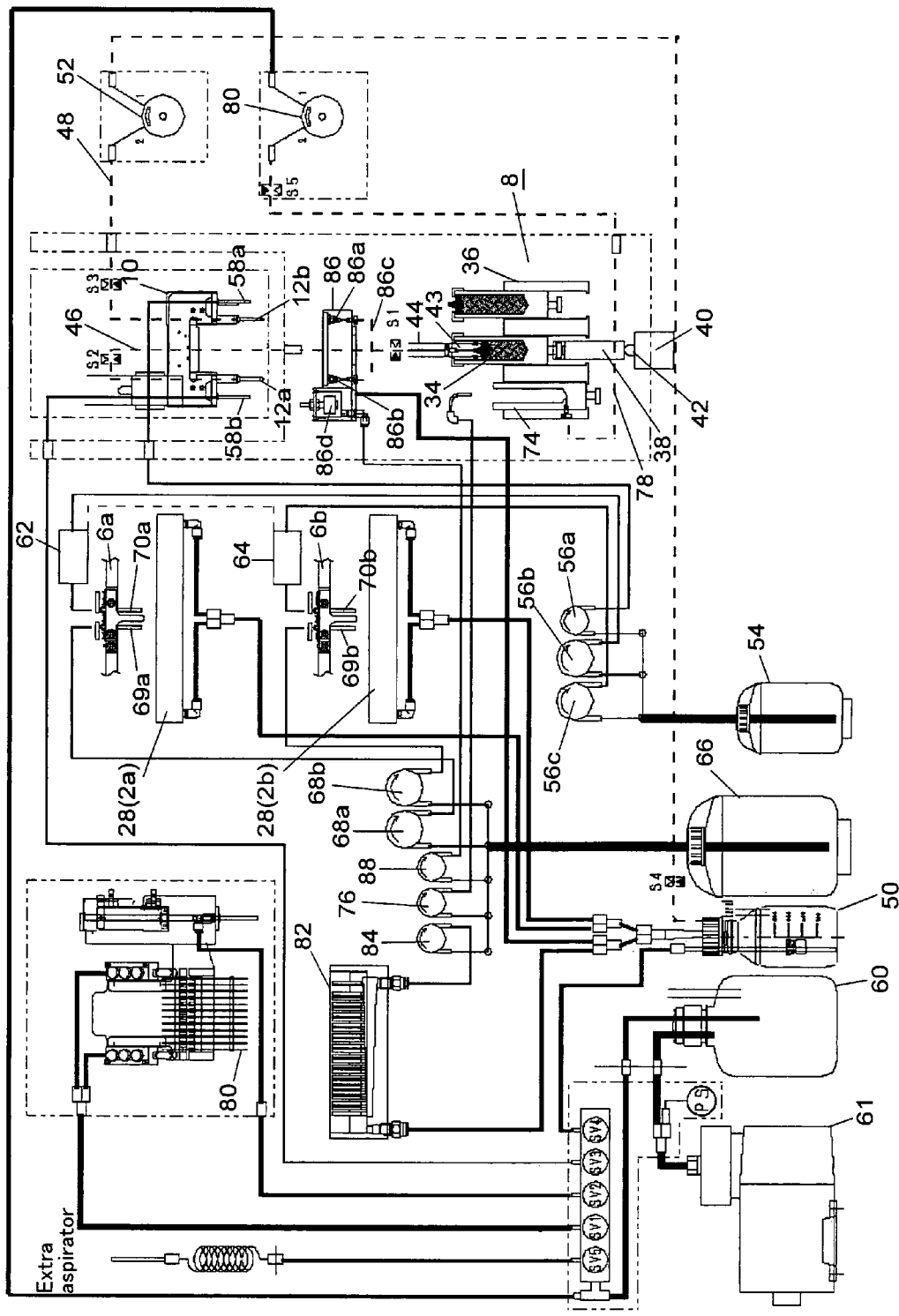
FIG. 5 is a view of flow channels for a loading medium, a loading buffer solution and washing water.
Figure 6A:
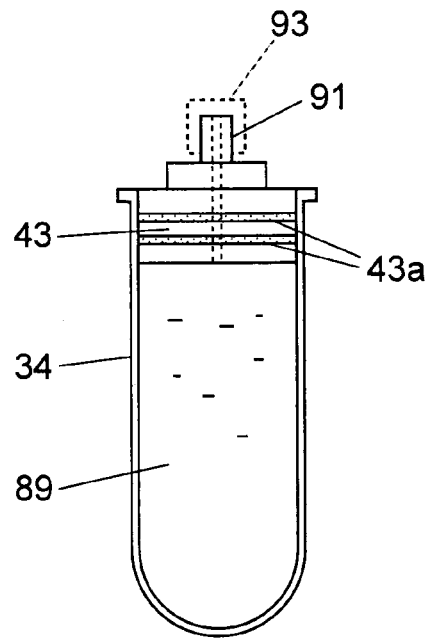
FIG. 6A is a section view showing a cartridge holding a loading medium.
Figure 6B:
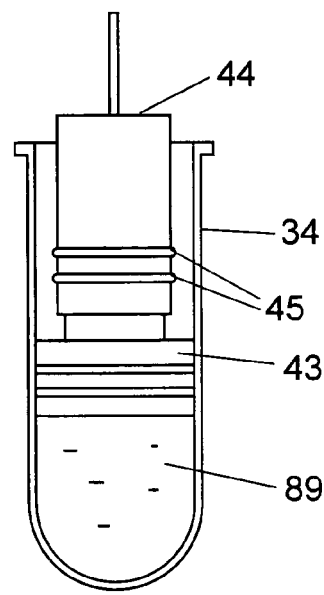
FIG. 6B is a section view of the cartridge in the state that the loading medium is sent out.
Figure 6B:

FIG. 5 shows a flow channel system for supplying a loading medium, a loading buffer solution and washing water, and discharging the excess loading buffer solution. The loading medium is held in the cartridge 34 as shown in FIG. 6A and FIG. 6B to be explained later and attached to the loading medium charging unit 8. A rack 36 of the loading medium charging unit 8 is capable of mounting two cartridges 34. Each cartridge 34 is moved to the position of an actuator 38 that pushes up the lower end by the rack 36.

Below the actuator 38, a charging lift arm 40 is provided. The charging lift arm 40 has in its upper end, a load cell 42, and the load cell 42 comes into abutment with a lower end of the actuator 38 and pushes up the actuator 38 via the load cell 42. The rack 36 is able to slide in the lateral direction in the figure, and position each of the two cartridges 34 at the position of the actuator 38.

The cartridge 34 positioned at the position of the actuator 38 is attached with a charging line connector 44, and is guided by the nozzle 12a of the nozzle mechanism 10 through a charging line 46 shown by broken lines. As shown in FIG. 4A, the nozzle 12a is inserted into one port 32a of the loading medium charging groove within the anode reservoirs 3a or 3b attached to the anode side of the electrophoresis plate in a liquid-tight manner, and the nozzle 12b is inserted into the other port 32b of the loading medium charging groove in a liquid-tight manner, whereby the pair of nozzles 12a and 12b connect with each other via the loading medium charging groove 30.

Returning to FIG. 5, the nozzle 12b is guided to a drain bottle 50 through a loading medium discharging line 48. The line 46 is provided with sensors S1, S2 for sensing a loading medium or water in the line, and the line 48 is provided with sensors S3, S4 for sensing a loading medium or water in the line and a 6-port valve 52 to control the opening/closing of the line 48.

For washing the loading medium charging line 46 and the discharging line 48, the rack 36 is provided with a charging line wash port 74, and the moving range of the rack 36 is set so that the wash port 74 can also be positioned at the position above the actuator 38. The wash port 74 is supplied with washing water in a water tank 66 by a peristaltic pump 76. Below the wash port 74, a disposal line 78 is provided for disposing the washing water remaining after use, and the disposal line 78 is guided to a vacuum tank 60 via a sensor S5 for sensing water in the line and a 6-port valve 80.

In washing the loading medium charging line 46 and the discharging line 48, the loading medium charging nozzle mechanism 10 is shifted to the charging line washing unit, which is illustrated by the reference numeral 86 below the nozzle mechanism 10 in the right part of FIG. 5, and the nozzles 12a, 12b are inserted into two ports 86a, 86b of the charging line washing unit 86. The ports 86a, 86b are connected by a shortcut line 86c, and by insertion of the nozzles 12a, 12b, a shortcut between the loading medium charging line 46 and the discharging line 48 is established. On the other hand, the charging line connector 44 is removed from a plunger lid 43 of the cartridge 34, and inserted into the wash port 74 that is displaced by the rack 36. Before insertion, washing water is applied to the wash port 74 by the peristaltic pump 76, while the 6-port valve 80 is closed. Then, in the same way as the case of charging the loading medium, the wash port 74 is pushed up by the actuator 38 and the charging lift arm 40, and the washing solution in the wash port 74 is led to the drain bottle 50 through the loading medium charging line 46, the shortcut line 86c, and the discharging line 48 because the O-ring is attached to the outer circumference of the distal end of the line connector 44 for keeping liquid tightness with the inner wall of the wash port 74. As the wash port is pushed up to a predetermined position, the 6-port valve 80 is opened, and the washing solution in the line is collected into the vacuum tank by a diaphragm pump. Since an end part of the discharging line 48 is situated in and above the drain bottle 50, and the drain bottle is opened to the atmospheric air, air is introduced into the line via the drain bottle 50 after collection of the washing solution in the line, and the line is dried. Washing and drying of the line are executed only at the time of replacement of a polymer cartridge. Timing for replacement of the polymer cartridge is sensed by the pushup position of the charging lift arm, which is automatically conducted. Further, the charging line washing unit 86 is supplied with water by a peristaltic pump 88 and its water level is kept constant by a float switch 86d. The loading medium charging nozzle mechanism 10 after completion of charging of the loading medium moves to the position where the distal ends of the nozzles 12a, 12b soak in the water of the charging line washing unit 86, whereby contact between the loading medium and air is prevented. This prevents the loading medium from drying and clogging in the nozzle and the line.

As a loading buffer supplying mechanism for supplying the reservoirs 28, 3 of the electrophoresis plates with a loading buffer solution, a buffer tank 54 holding the loading buffer solution and peristaltic pumps 56a, 56b, 56c for sending the liquid are provided. The peristaltic pumps 56a, 56b, 56c are disposed in the pump mechanism 20.

The line that supplies a loading buffer solution by means of the pump 56a leads to the nozzle 58a provided in the nozzle mechanism 10, and the nozzle 58a is inserted in the reservoir 3 of the anode side and the loading buffer solution is supplied to the reservoir 3. Into the reservoir 3, the other nozzle 58b provided in the nozzle mechanism 10 is also inserted, and the line leading to the nozzle 58b is guided and aspirated to the vacuum tank 60 via an electromagnetic valve SV3, and the used loading buffer solution is disposed before the loading buffer solution is supplied. The nozzles 58a, 58b of the loading buffer solution supplying line are provided in the nozzle mechanism 10, so that they are commonly used for the anode-side reservoirs 3 of the electrophoresis plates on both of the platens 2a, 2b.

The reference numeral 61 denotes a diaphragm pump for carrying out aspiration by reducing the pressure in the interior of the vacuum tank 60.

The line that leads to the pump 56b of the loading buffer solution supplying mechanism is guided to the cathode-side reservoir 28 of the electrophoresis plate on one platen 2a while its temperature is kept at a predetermined temperature by a preheater 62. Further, the line that leads to the other pump 56c is guided to the cathode-side reservoir 28 of the electrophoresis plate on the other platen 2b via a preheater 64.

In order to wash the cathode-side reservoirs 28, 28 of the electrophoresis plates on both of the platens 2a, 2b, a flow channel that guides the washing water from the water tank 66 to the cathode-side reservoir 28 of the electrophoresis plate on one platen 2a via a peristaltic pump 68a, and a nozzle 69a are provided, and a flow channel that guides the washing water to the cathode-side reservoir 28 of the electrophoresis plate on the other platen 2b via a peristaltic pump 68b, and a nozzle 69b are provided.

Nozzles 70a, 70b for guiding the loading buffer solution and the nozzles 69a, 69b for guiding the washing water to the cathode-side reservoirs 28 on the electrophoresis plates on both of the platens 2a, 2b are provided integrally with the electrodes 6a, 6b for the respective cathode-side reservoirs 28, so that they are movable in the vertical direction above the respective electrophoresis plates and are inserted into the reservoirs 28, 28 together with the electrodes 6a, 6b in a detachable manner. The electrodes 6a, 6b are electrically connected to the flow channels 24 of the respective electrophoresis plates via the loading buffer solution in the reservoirs 28, 28 of the respective electrophoresis plates.

As illustrated in the upper left part in FIG. 5, in order to aspirate and dispose the excess loading medium accumulating at the sample dispensing opening 24a in the cathode-side reservoir 28 of the electrophoresis plate, an aspirator 80 is arranged above the platens 2a, 2b so as to be movable in the vertical direction. The aspirator 80 has nozzles that are arranged at the same pitch with or n-times (n is an integer) the pitch of the sample dispensing openings 24a, and these nozzles are guide to the vacuum tank 60 via an aspirating line having an electromagnetic valve SV1. The aspirator 80 is supported to be movable also in the horizontal direction so that it can be commonly used by the electrophoresis plates on both of the platens 2a, 2b.

The member seen below the aspirator 80 in FIG. 5 and denoted by the reference numeral 82 is a wash port for washing the dispensing tip of the pipetter mechanism 14 as will be illustrated in detail in FIG. 8. The wash port 82 has holes at a pitch corresponding to the nozzles of the pipetter mechanism 14 or at a pitch of n times (n is an integer) the same, and the holes are supplied with the washing solution from the water tank 66 via a peristaltic pump 84, and the washing solution after washing is discharged to the drain bottle 50.

Also the peristaltic pumps 68a, 68b, 76, 84, 88 are provided in the pump mechanism 20.

FIG. 6A and FIG. 6B show the details of the cartridge 34 that holds the loading medium. As shown in FIG. 6A, the main body of the cartridge 34 is a cylindrical container which opens in its top part, and the cartridge 34 before use holds a loading medium 89, and the plunger lid 43 is slidably fitted into the opening at the upper end of the cartridge 34 in a liquid-tight manner via a sealing member 43a such as an O-ring. The center of the plunger lid 43 is pierced into a through-hole, and the top face thereof is provided with a pickup port 91 leading to the through-hole. The pickup port 91 is closed by a cap 93 before use.

The cartridge 34 is attached to the rack 36 of the loading medium charging unit 8, and the cap 93 is removed. The loading medium charging unit 8 is also provided with a mechanism that automatically removes the cap 93. To the pickup port 91 after removal of the cap 93, a charging line connector 44 is attached as shown in FIG. 6B. To the charging line connector 44, an O-ring 45 is fitted so that it can slide in a liquid-tight manner when the connector is inserted into the wash port 76.

For supplying the loading medium, in the condition that the pickup port 91 is attached with the charging line connector 44, and the plunger lid 43 is fixed to the rack 36, the cartridge 34 is pushed upward via the actuator 38 by the charging lift arm 40 as shown in FIG. 6B. Since the position of the plunger lid 43 is fixed, the plunger lid 43 is relatively pushed down in the cartridge 34 as the cartridge is pushed up, so that the loading medium 89 is supplied to the charging line from the hole of the plunger lid 43 via the connector 44.

Returning to FIG. 5, since the charging lift arm 40 has the load cell 42 on the contacting surface with the actuator 38 pushing up the cartridge 34, the pressure of pushing up the cartridge 34 is detected by the load cell 42, so that charging pressure of the loading medium can be controlled, and abnormal conditions such as clogging in the loading medium charging line 46 or the discharging line 48 can be monitored based on the detected pressure.

Figure 7:
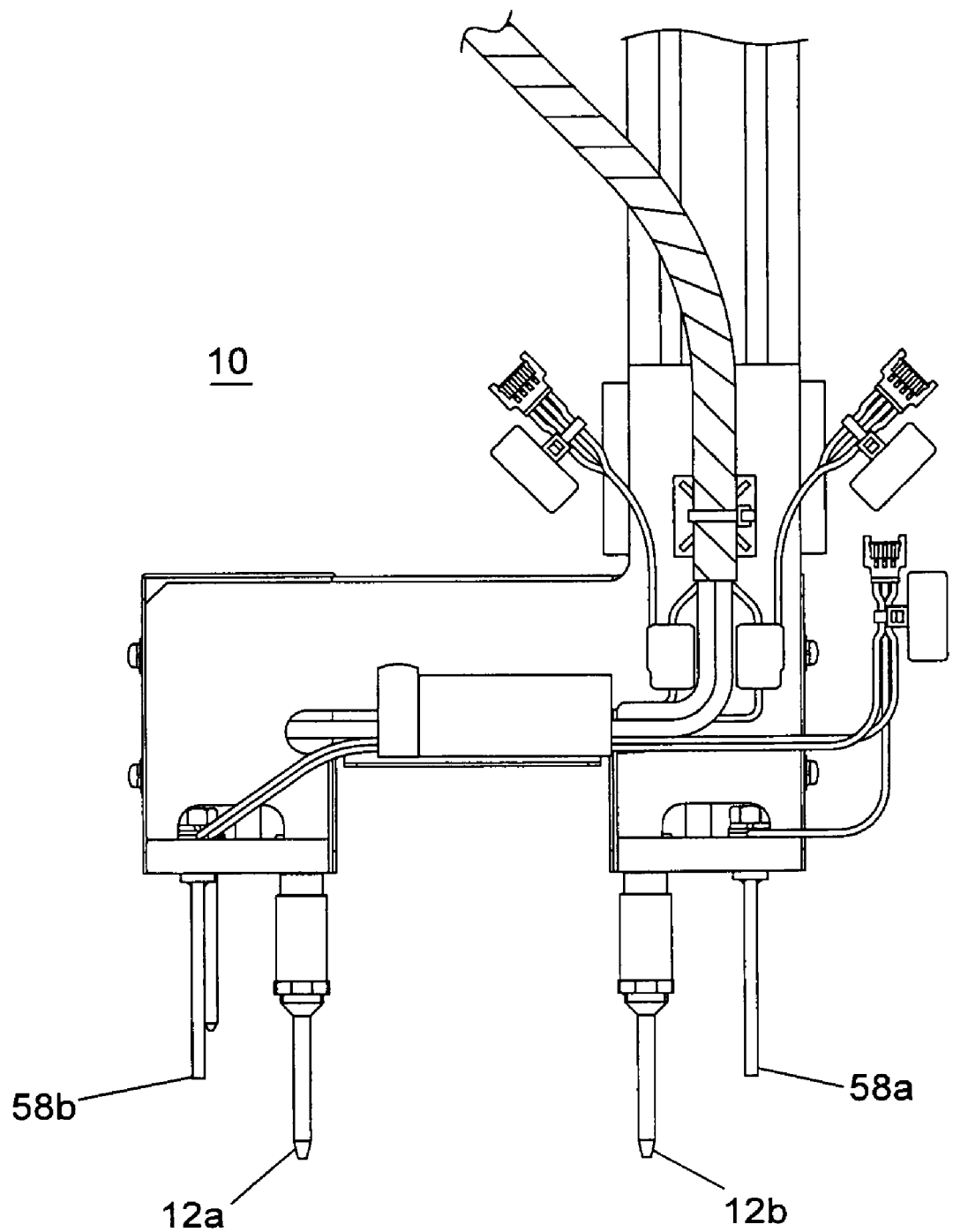
FIG. 7 is a front view showing the details of a nozzle mechanism 10.

FIG. 7 shows the details of the nozzle mechanism 10. The pair of nozzles 12a, 12b attached to the nozzle mechanism 10 are connected to the loading medium charging unit 8, and inserted in a liquid-tight manner into the ports 32a, 32b of the loading medium charging groove 30 within one of the anode reservoirs 3a, 3b of the electrophoresis plates respectively placed on the platens 2a, 2b. These nozzles 12a, 12b are movably supported between the port positions of the respective electrophoresis plates placed on the two platens 2a, 2b. To the nozzle mechanism 10, also attached are a loading buffer solution applying nozzle 58a, and a loading buffer solution collecting nozzle 58b, and these nozzles 58a, 58b are also moved between the reservoirs 3a, 3b of the electrophoresis plates placed on the two platens 2a, 2b together with the nozzles 12a, 12b.

Figure 8A:
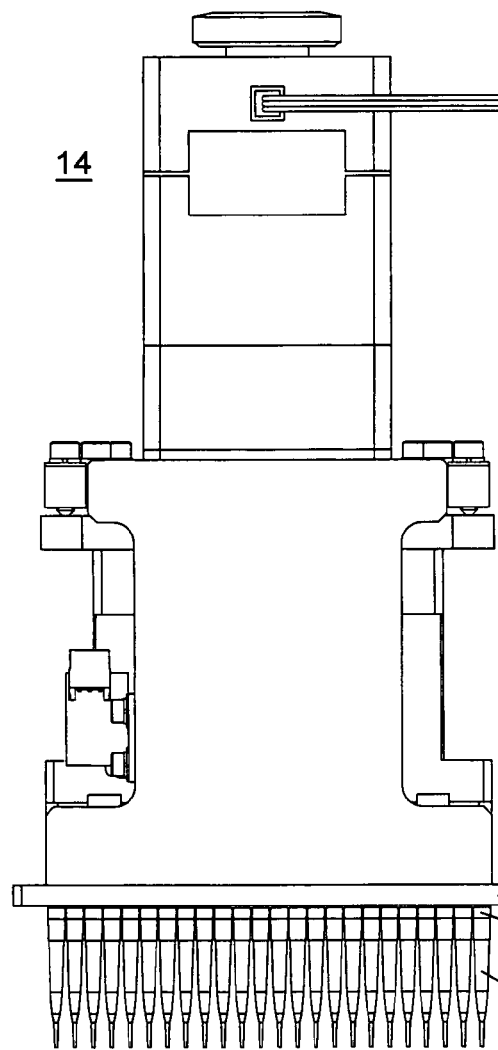
FIG. 8A is a front view showing a pipetter mechanism.
Figure 8B:
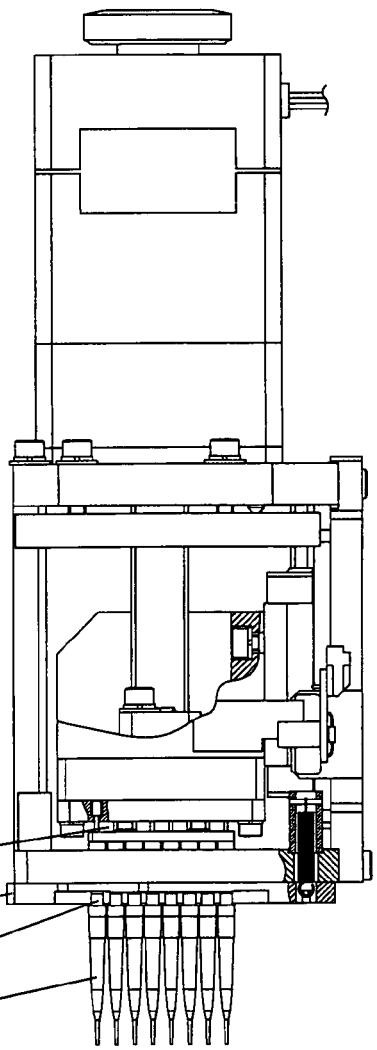
FIG. 8B is a lateral section view of the same.

FIG. 8A and FIG. 8B show the details of the pipetter mechanism 14 for dispensing samples to the sample dispensing openings 24a of the electrophoresis plates placed on the platens 2a, 2b. FIG. 8A is a front view, and FIG. 8B is its lateral section view. The pipetter mechanism 14 has in its distal end, 192 pipettes 90 arranged in the same arrangement with the sample dispensing openings 24a, and the pipettes 90 are connected, in their proximal ends, with respective dispenser plungers 96, whereby aspiration and discharge of samples are conducted. To each pipette 90, a disposable dispensing tip 92 is attached in a detachable manner for use in dispensing the sample.

An arrangement of the pipettes 90 also coincides with an arrangement of sample holding wells of the sample plate, and 192 samples can be aspirated at once by one sample aspirating operation. In the reservoir 28 of the electrophoresis plate, since 384 sample dispensing openings 24a are arranged in the same arrangement with the pipettes 90, two sample dispensing operations by the pipetter mechanism 14 achieve application of samples into the 384 sample dispensing openings 24a.

The pipetter mechanism 14 has, on the proximal end side of the pipettes 90, a tip remover plate 94 serving as a detaching mechanism for removing the dispensing tips 92 from the pipettes 90. The tip remover plate 94 is formed with holes which are larger than the contour of the proximal end of the pipette 90 but smaller than the contour of the proximal end of the dispensing tip 92, in the same arrangement with that of the pipettes 90, and fitted into the pipettes 90 on the proximal end side of the dispensing tips 92. The dispensing tips 92 are detached from the pipettes 90 by pushing out the tip remover plate 94 in the distal end direction of the pipettes 90.

The displacement mechanism of the pipetter mechanism 14 is designed to be able to displace the pipettes 90 to the position of sample dispensing openings 24a of each of the electrophoresis plates placed on the two platens 2a, 2b, the sample aspirating position where the samples are aspirated from the sample plate, the position where the dispensing tips 92 before attachment are arranged, and the position where the dispensing tips are disposed, in addition to the vertical movement.

In the position of the sample dispensing opening 24a and in the sample aspirating position, dispensing of samples can be executed by aspiration and discharge of the samples by the dispenser plunger 96. Further, in the position where the dispensing tips 92 are arranged, the dispensing tips 92 are attached to the pipettes 90 by descending the pipettes 90 toward the dispensing tips 92, and in the position where the dispensing tips 92 are disposed, the dispensing tips 92 are detached from the pipettes 90 and disposed by the tip remover plate 94. In this manner, attachment/detachment of the dispensing tips 92 to/from the pipettes 90 can be automated.

Figure 9A:
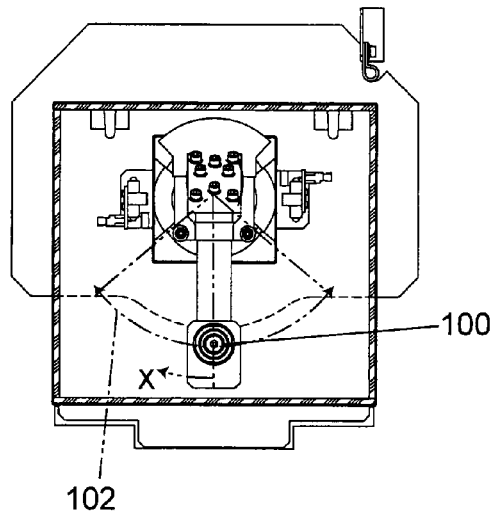
FIG. 9A is a plan view showing a detector.
Figure 9B:
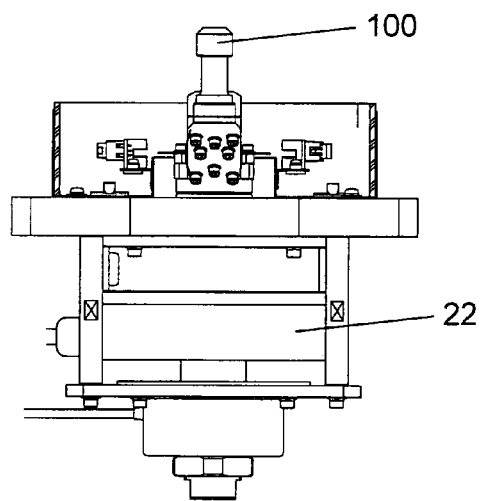
FIG. 9B is a front view of the same.
Figure 9C:
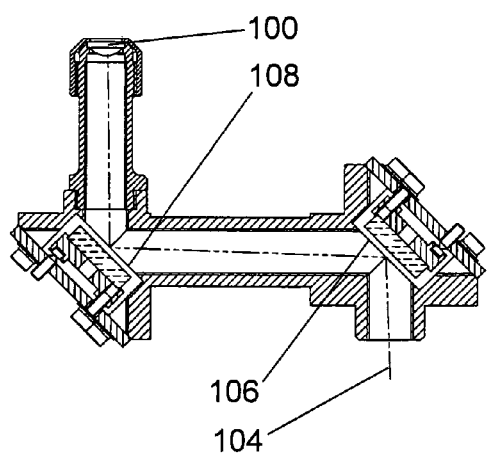
FIG. 9C is a section view along the line X-X of FIG. 9A.

FIG. 9A, FIG. 9B and FIG. 9C show the detector. Although two detectors provided respectively below the platens 2a, 2b are illustrated, the explanation will be made for one of them because they have the same structure. FIG. 9A is a plan view, FIG. 9B is a front view, and FIG. 9C is a section view along the line X-X of FIG. 9A.

In the electrophoresis plates placed on the platens 2a, 2b, the anode side of the electrophoresis flow channel 24 is a detecting position, and each of the platens 2a, 2b is provided with a window for optical detection by the detector disposed under the respective detecting position.

The detector includes a spinner head 100 having a lens constituting an epi-illumination optical system that focuses and projects exciting light to the electrophoresis flow channel 24 in the detecting position of the electrophoresis plate placed on the platen, and receives fluorescence generated from the components moving along each electrophoresis flow channel upon irradiation by the exciting light. The detector also includes a servo motor 22 as a scanning mechanism that causes the spinner head 100 to move reciprocatingly along an arc 102 in a plane parallel with the electrophoresis plate so that it traverses the electrophoresis flow channel. For constituting the optical system, also provided are an exciting optical system for generating exciting light and a light-receiving optical system for receiving fluorescence and detecting it while separating into four kinds of wavelengths. However, they are not illustrated in FIGS. 9A, 9B and 9C.

The servo motor 22 of the scanning mechanism that is a driving source for reciprocating movement of the spinner head 100 is a hollow servo motor having a hollow rotary center, and the hollow space of the hollow servo motor 22 forms an optical path 104 linking the spinner head 100 to the exciting optical system and the light-receiving optical system. In FIG. 9C, the hollow servo motor 22 is not seen in the figure; however, it is arranged on the lower side, and the optical path 104 passing through the hollow space of the hollow servo motor 22 is bent by mirrors 106, 108 arranged within the hollow member driven by the servo motor 22. In this manner, the spinner head 100 are connected to the exciting optical system and the light-receiving optical system.

The exciting optical system and the light-receiving optical system are shown in FIG. 10. The exciting optical system and the light-receiving optical system are disposed on the optical path 104 in the lower part of FIG. 9C. A light source of the exciting optical system is, for example, laser, and on an optical path of a laser beam 110 of the exciting light is arranged a dichroic mirror 112. On a reflecting optical path of the dichroic mirror 112, a dichroic mirror 118 is disposed via an exciting light cut filter 114 and a lens 116, and at the position where the transmitted light of the dichroic mirror 118 is received, a photomultiplier tube is disposed as a light detector 124. The lens 116 is provided for collecting fluorescence to a photoelectric face of a photomultiplier tube of the light detector 124 and light detectors 126, 128, 130 as will be described later. On a reflecting optical path of the dichroic mirror 118, a dichroic mirror 120 is disposed, and at the position where transmitted light of the dichroic mirror 120 is received, a photomultiplier tube is disposed as the light detector 126. On a reflecting optical path of the dichroic mirror 120, a dichroic mirror 122 is disposed, and at the position where transmitted light of the dichroic mirror 122 is received, a photomultiplier tube is disposed as the light detector 130. At the position where the reflected light of the dichroic mirror 122 is received, a photomultiplier tube is disposed as the light detector 128.

Examples of optical characteristics of an exciting light source, labeling dyes for samples to be loaded, and each optical element will be shown below. As an exciting light source, argon laser is used, and a laser beam at 488 nm generated thereby is used as exciting light. As labeling dyes, four kinds of fluorescent pigments, that is, dR110 (wavelength of generating fluorescence is 530 nm to 535 nm), dR6G (wavelength of generating fluorescence is 560 nm to 565 nm), dTAMURA (wavelength of generating fluorescence is 590 nm to 595 nm) and dROX (wavelength of generating fluorescence is 615 nm to 620 nm) are used.

When as the dichroic mirror 112, a mirror adapted to permit transmission of light having a shorter wavelength than 520 nm and to reflect light having a longer wavelength is used, exciting light at 488 nm is caused to transmit to make the fluorescence from the used labeling dye to be reflected. When a cut filter that blocks light having a shorter wavelength than 525 nm and permits transmission of light having a longer wavelength is used as the cut filter 114, the exciting light component is blocked to allow transmission of fluorescence.

When a dichroic mirror adapted to permit transmission of light having a longer wavelength than 600 nm and to reflect light having a shorter wavelength is used as the dichroic mirror 118, the fluorescence having transmitted through the dichroic mirror 118 and detected by the light detector 124 is only fluorescence that is generated from the dROX.

When a dichroic mirror adapted to permit transmission of light having a longer wavelength than 575 nm and to reflect light having a shorter wavelength is used as the dichroic mirror 120, the fluorescence having transmitted through the dichroic mirror 120 and detected by the light detector 126 is fluorescence ranging from 575 nm-600 nm, that is generated from the dTAMURA.

When a dichroic mirror adapted to permit transmission of light having a longer wavelength than 545 nm and to reflect light having a shorter wavelength is used as the dichroic mirror 122, the fluorescence having transmitted through the dichroic mirror 122 and detected by the light detector 130 is fluorescence ranging from 545 nm-575 nm, that is generated from the dR6G.

Further, since fluorescence reflected by the dichroic mirror 122 and detected by the light detector 128 has a wavelength shorter than 545 nm, it is only the fluorescence that is generated from the dR110.

The exciting light from the exciting light source transmits through the dichroic mirror 112 and is guided to the spinner head 100 along the optical path 104, and is emitted to the detecting position of the electrophoresis plate placed on the platen from the spinner head 100. Fluorescence generating at the detecting position of the electrophoresis plate is returned to the dichroic mirror 112 from the spinner head 100 along the optical path 104, and is reflected by the dichroic mirror 112. Then, the fluorescence is separated into fluorescence from four kinds of labeling dyes by the dichroic mirrors 118, 120, 122 after removal of the exciting light component by the cut filter 114, and detected by the respective light detectors 124, 126, 128, 130.

Next, operation of electrophoresis analysis according to the present embodiment will be explained.

(Attachment of Electrophoresis Plate)

Electrophoresis plates are placed on the platens 2a, 2b, and marks on the electrophoresis plates are aligned with marks 4 on the platens 2a, 2b to achieve positioning. By a temperature regulation mechanism of the platens 2a, 2b, temperature of the electrophoresis plates are kept constant (Charging of Loading Medium)

The cartridge 34 holding a loading medium is attached to the loading medium charging unit 8, and the charging line connector 44 is connected to the cartridge 43. The nozzles 12a, 12b of the nozzle mechanism 10 are inserted into the ports 32a, 32b of the loading medium charging groove in the anode-side reservoir 3 of the electrophoresis plate placed on either one of the platen 2a or 2b. Here, first, the electrophoresis plate on the platen 2a is charged with the loading medium.

The loading medium discharging line 48 is made into the condition where it is guided to the drain bottle 50 by the 6-port valve 52, and the loading medium in the cartridge 34 is guided to the loading medium charging groove 30 of the electrophoresis plate from the nozzle 12a through the charging line 46 via the port 32a by ascending of the charging lift arm 40.

After the loading medium moves through the loading medium charging groove 30 from the port 32b, and spills into the loading medium discharging line 48 via the nozzle 12b, the 6-port valve 52 is closed. The position of the leading end of the loading medium in the line is sensed by the sensors S1 to S3, and the timing at which the 6-port valve 52 is switched over is determined. As a result of closing the 6-port valve 52, the loading medium is put into the electrophoresis flow channels 24 from the loading medium charging groove 30 under pressure. Upon spilling of the loading medium into the sample dispensing openings 24a within the cathode-side reservoir 28, supply of the loading medium from the cartridge 34 is stopped.

During charging of the loading medium, the loading buffer used in the previous measurement and remaining in the anode reservoir 3 is collected into the vacuum tank 60 through the nozzle 58b by opening the electromagnetic valve SV3. Then, a fresh loading buffer is supplied by the pump 56a through the nozzle 58a. After completion of charging, the nozzles 12a, 12b of the loading medium charging nozzle mechanism 10 are pulled out of the ports 33a, 33b of the anode reservoir 3, and at this time, the loading buffer within the reservoir enters the ports 33a, 33b, and comes into contact with the loading medium in the loading medium charging groove 30. The loading medium charging nozzle mechanism 10 moves to the position where the distal ends of the nozzles 12a, 12b soak in the water in the charging line washing unit 86.

Concurrent with the above, the aspirator 80 is inserted into the sample dispensing opening 24a, and the loading medium spilling into the opening 24a is aspirated and removed. This completes the charging operation of the loading medium to the electrophoresis plate on the platen 2a.

In the electrophoresis plate (platen 2a side) charged with the loading medium, the line leading to the pump 56b of the loading buffer solution supplying mechanism is guided to the cathode-side reservoir 28 and the loading buffer solution is supplied. On the cathode side, the loading buffer solution is supplied to the reservoir 28 while it is kept at a pre-determined temperature by the preheater 62.

(Pre-Electrophoresis)

In order to remove ion substances in the loading medium, pre-electrophoresis is carried out. Upon insertion of an electrode into the cathode-side reservoir 28, an electric connection is established via the loading buffer between the electrode and the electrode in the anode-side reservoir 3. Then, a predetermined loading voltage is applied between the electrode inserted into the cathode-side reservoir 28 and the electrode in the anode-side reservoir 3.

(Sample Application)

A sample plate holding samples to be subjected to electrophoresis is sent out to the sample aspirating position from the stacker mechanism 16 and positioned at that position. While the sample plate is sent to the sample aspirating position, the sealing member is punched with a punching mechanism, and a barcode is read by the barcode reading mechanism.

After the pipetter mechanism 14 moves to the sample aspirating position and aspirates a predetermined amount of samples from the sample plate by means of the dispensing tips 92 attached to the pipettes 90 of the pipetter mechanism 14, the aspirator 80 moves to the sample dispensing openings 24a of the electrophoresis plate on the platen 2a, removes the loading buffer within the openings 24a, and then the pipetter mechanism 14 moves to the sample dispensing openings 24a of the electrophoresis plate on the platen 2a and applies the samples to the openings 24a from the dispensing tips 92.

Thereafter, the dispensing tips 92 of the pipetter mechanism 14 are inserted into the wash ports 82 and washed to be ready for the next application of a sample. In this context, a sample dispensing operation by the pipetter mechanism 14 is repeated twice to complete the sample dispensing of one electrophoresis plate.

(Sample Injection)

Distal ends of 384 electrodes of a cathode electrode 6 are soaked into the samples applied to the sample dispensing openings 24a. A predetermined voltage is applied between the cathode electrode and the anode electrode incorporated into the anode reservoir 3 and the samples are introduced to the loading medium in the electrophoresis flow channel 24.

(Removal of Sample)

After removing the sample remaining in the sample dispensing openings 24a by aspirating by the aspirator 80, water is discharged or aspirated in the openings 24a by means of the pipetter mechanism 14 to achieve washing. Thereafter, the loading buffer is supplied into the cathode reservoir 28 by means of the pump 56b.

This is the end of the pretreatment in the electrophoresis plate on one platen 2a, and the electrophoresis separation is conducted on this electrophoresis plate. In electrophoresis separation, the cathode electrode 6 is inserted into the cathode-side reservoir 28 of the electrophoresis plate, and is electrically connected with the electrophoresis flow channels via the loading buffer solution. Electric power is supplied to these electrodes from the power unit to initiate the electrophoresis.

Upon completion of the pretreatment at the electrophoresis plate on one platen 2a, the pretreatment at the electrophoresis plate on the other platen 2b is started. The pretreatment at the electrophoresis plate on the platen 2b is started without waiting for the completion of the electrophoresis operation in the electrophoresis plate on the platen 2a. The operation of the pretreatment at the electrophoresis plate on the platen 2b is the same as the pretreatment operation at the electrophoresis plate on the platen 2a described above.

The pretreatment at the electrophoresis plate on the platen 2b ends immediately before completion of the electrophoresis operation at the electrophoresis plate on the platen 2a, and after completion of the electrophoresis operation, electrophoresis operation at the electrophoresis plate on the platen 2b is started. In this manner, timing of starting the pretreatment is controlled by a computer so that the pretreatment at the electrophoresis plate on one of the platens completes immediately before completion of the electrophoresis operation at the electrophoresis plate on the other one of the platens.

(Detection)

At the detecting positions of the electrophoresis plates on the platens 2a, 2b, exciting light from the respective optical detector is emitted, and fluorescence from the samples having migrated thereto are detected, and base sequences are determined.

In an electrophoresis plate after completion of the measurement, the used loading medium is replaced by a fresh loading medium by repetition of the pretreatment, and analysis of new samples is repeated.

The electrophoresis apparatus of the present invention may be used for electrophoretically separating a very small amount of protein, nucleic acid and drug with high speed and high resolution in biochemical, molecular biological or clinical fields.

What is claimed is:

1. An electrophoresis apparatus for carrying out electrophoresis using an electrophoresis plate comprising:

two platens on each of which the electrophoresis plate can be respectively placed, the two platens being able to control temperature of the placed electrophoresis plates, each of the electrophoresis plate including a substrate with a plurality of electrophoresis flow channels formed therein, and a pair of anode-side and cathode-side reservoirs disposed at both end parts of the electrophoresis flow channels, the reservoirs holding a loading buffer solution and electrically communicating at their bottom parts with the end parts of the electrophoresis flow channels via the loading buffer solution, wherein sample dispensing openings leading to first ends of the electrophoresis flow channels are disposed within the cathode-side reservoir, a loading medium charging groove leading to second ends of the electrophoresis flow channels is formed within the anode-side reservoir, and ports opening into the anode-side reservoir are formed on both ends of the loading medium charging groove;

a loading medium charging unit for sending a loading medium under pressure;

a loading medium charging nozzle mechanism having a pair of nozzles and supporting the nozzles movably between the ports of the electrophoresis plates placed on the two platens, the nozzles being inserted into the ports in a liquid-tight manner and being connected to the loading medium charging unit;

a pipetter mechanism including a plurality of pipettes for dispensing samples to the sample dispensing openings of one of the electrophoresis plates placed on the platens, and a displacement mechanism that displaces the pipettes between positions of the sample dispensing openings of the electrophoresis plates placed on the platens and a sample aspirating position at which samples are aspirated from the sample plate;

a stacker mechanism for storing sample plates holding samples, and sending out a selected one sample plate to the sample aspirating position;

a loading buffer solution supplying mechanism for supplying a loading buffer solution;

a loading buffer solution dispensing mechanism connected to the loading buffer solution supplying mechanism for applying the loading buffer solution to the reservoirs of the electrophoresis plates placed on the two platens:

a power unit that applies voltage to the electrophoresis flow channels for each of the electrophoresis plates placed on the platens to cause electrophoresis separation; and a detector that optically detects components migrating along each electrophoresis flow channel at a detecting position set for the anode side of the electrophoresis plates placed on the two platens.

2. The electrophoresis apparatus according to claim 1, wherein a pitch at which the sample dispensing openings are arranged in the electrophoresis plate is 1/n (n is an integer) of a pitch of sample holding wells of the sample plate.

3. The electrophoresis apparatus according to claim 1, wherein the platens and the electrophoresis plates are provided with a mark or a mechanism for mutual positioning.

4. The electrophoresis apparatus according to claim 1,
wherein the loading medium charging unit is adapted to receive a cartridge holding a loading medium, the cartridge has a plunger lid in its upper part, which is connected to the nozzles of the loading medium charging nozzle mechanism, and the loading medium in the cartridge is sent under pressure as the plunger lid is relatively pushed down into the cartridge main body, and the loading medium charging unit has a mechanism for fixing the plunger lid and a charging lift arm for pushing up the cartridge main body so as to relatively push down the plunger lid into the cartridge main body.

5. The electrophoresis apparatus according to claim 4, wherein the charging lift arm has a load cell in an abutment portion on the cartridge main body side, and detects pressure during charging of the loading medium by the load cell.

6. The electrophoresis apparatus according to claim 1, wherein the detector includes:

a spinner head having a lens constituting an epi-illumination optical system that focuses and projects exciting light to each electrophoresis flow channel in the detecting positions of the electrophoresis plates placed on the platens, and receives fluorescence generated from the components moving along each electrophoresis flow channel upon irradiation with the exciting light;

a scanning mechanism that causes the spinner head to move reciprocatingly along an arc in a plane which is parallel with the electrophoresis plate, so that it traverses the electrophoresis flow channels;

an exciting optical system for generating the exciting light; and a light-receiving optical system that receives fluorescence and detects it while separating into four kinds of wavelengths, and wherein the scanning mechanism has a hollow servo motor having a hollow space as its rotation axis, as a driving source of the reciprocating movement, and the hollow space of the hollow servo motor forms an optical path connecting the spinner head to the exciting optical system and the light-receiving optical system.

7. The electrophoresis apparatus according to claim 6, wherein a light source of the exciting optical system is laser, and the light-receiving optical system has one rejection filter for removing an exciting light component and three dichroic mirrors for separating the fluorescence into four kinds of wavelengths.

8. The electrophoresis apparatus according to claim 1, wherein the pipetter mechanism is so designed that a disposable dispensing tip is detachably attached to each pipette, and has a detaching mechanism for detaching the dispensing tips from the pipettes, and the displacement mechanism of the pipetter mechanism is structured to be able to displace the pipette also to a position where the dispensing tips are arranged and a position where the dispensing tips are disposed, whereby at the position where the dispensing tips are arranged, the dispensing tips are attached to the pipettes by descending the pipettes toward the dispensing tips, while at the position where the dispensing tips are disposed, the dispensing tips are detached from the pipettes by the detaching mechanism.

9. The electrophoresis apparatus according to claim 8, further comprising an automatic water feed type wash port for washing the dispensing tips attached to the pipetter mechanism.

10. The electrophoresis apparatus according to claim 1, wherein a surfaces of each of the sample plates stored in the stacker mechanism is covered with a sealing member for preventing samples from vaporizing, and the stacker mechanism has a punching mechanism that punches the scaling member in transferring the sample plate to the sample aspirating position.

11. The electrophoresis apparatus according to claim 1, wherein each of the sample plate stored in the stacker mechanism has a barcode representing information about samples, pasted thereto, and the electrophoresis apparatus further comprises a barcode reading mechanism that reads the barcode before dispensing the samples.

12. The electrophoresis apparatus according to claim 1, wherein liquid sending means in the loading buffer solution supplying mechanism are peristaltic pumps.

13. The electrophoresis apparatus according to claim 1, wherein the loading buffer solution dispensing mechanism has a liquid level sensing means, and the liquid level sensing means is a capacitance type liquid level sensor made up of two dielectric plate members.

14. The electrophoresis apparatus according to claim 1, wherein the loading buffer solution dispensing mechanism has a heating and temperature control mechanism in the course of a flow channel through which the loading buffer solution is sent.

* * * * *